United States Patent [19]

Patel et al.

[11] Patent Number: 4,755,433
[45] Date of Patent: Jul. 5, 1988

[54] COVER FILM ON LIPSTICK SAMPLER

[75] Inventors: Vinu Patel, Oakdale; Robert W. H. Chang, Roseville, both of Minn.

[73] Assignee: Minnesota Mining and Manufacturing Company, St. Paul, Minn.

[21] Appl. No.: 925,828

[22] Filed: Oct. 30, 1986

[51] Int. Cl.$^4$ .................. B32B 27/00; A61K 7/021
[52] U.S. Cl. .................................. 428/422; 428/212; 428/484; 428/511; 424/63; 132/88.7
[58] Field of Search .................... 428/212, 424.2; 132/88.7; 424/63

[56] References Cited

U.S. PATENT DOCUMENTS

| | | | |
|---|---|---|---|
| 3,936,559 | 2/1976 | Newman | 428/212 |
| 4,403,963 | 9/1983 | Yoshida et al. | 434/100 |
| 4,507,382 | 3/1985 | Rousseau et al. | 430/275 |
| 4,529,658 | 7/1985 | Schwartz et al. | 428/421 |
| 4,611,611 | 9/1986 | Beal, Jr. | 132/88.7 |

Primary Examiner—John E. Kittle
Assistant Examiner—Patrick J. Ryan
Attorney, Agent, or Firm—Donald M. Sell; James A. Smith; Mark A. Litman

[57] ABSTRACT

Wax-base or emollient-base cosmetic compositions may be provided as samples on paper carrying sheets by providing the paper with materials that prevent absorption of oleic materials and providing the cosmetic compositions with a lower sheet that is oleophobic. A binder layer of an oleophilic wax or polymer may be used between said paper and the cosmetic composition. A frangible, thin polymeric film is placed over the cosmetic composition to prevent shear forces and pressure from smearing the composition.

22 Claims, No Drawings

COVER FILM ON LIPSTICK SAMPLER

BACKGROUND OF THE INVENTION

1. Field of the Invention

Cosmetic compositions having a wax or emollient base are provided in a structure suitable for sampling which is a multilayered article comprising a paper carrying sheet using (a) chemical impregnants which prevent absorption of oleic materials, (b) a polymeric material in contact with the surface of the cosmetic composition, and (c) an oleophilic film layer between said oleophilic surface and said cosmetic composition.

2. Background of the Art

Cosmetic samples of wax- or emollient-base compositions are often provided to the potential consuming public in conventional commercial forms. Lipstick tubes are available for general use at the sales counter as are bottles of foundation and other cosmetics. The open and general use of these samples by the public at large offers some potential health risks which should be avoided.

U.S. patent application Ser. No. 900,749, filed on Aug. 27, 1986, titled Cosmetic Sampling Device discloses a multilayered structure for sampling cosmetic compositions comprising a paper base having an oleophobic agent within said paper, a solid cosmetic composition layer containing a wax or emollient component on at least a portion of one surface of said paper base and an oleophilic surface in contact with said solid cosmetic composition layer.

SUMMARY OF THE INVENTION

Samples of solid cosmetic compositions having a wax or emollient carrying medium can be provided on paper carrying sheets. The paper is preferably impregnated or coated with a material that prevents absorption of oleic materials. A thin, frangible polymeric overcoat layer is used over the cosmetic composition to provide protection to the composition from pressure and temperature.

DETAILED DESCRIPTION OF THE INVENTION

Wax-base and emollient-base solid cosmetic compositions are not stable when coated in paper bases and therefore can not readily be sampled in that manner. The hydrocarbon, oleic, or lower molecular oleophilic materials seep into the paper and leave behind a cosmetic composition with less than optimal properties. Additionally, the appearance of oil stains around the cosmetic composition from that seepage is less than attractive to the potential buyer. Commercially available papers which are treated with polymeric and particulate compositions to prevent oil penetration have not been able to prevent penetration by these cosmetic compositions.

The use of penetrating compositions which are oleophobic has proved to be very useful in the solution of one aspect of this problem. These compositions should penetrate into the surface and preferably all the way through the paper to provide oleophobic properties. To be considered oleophobic, the treated paper should be able to be melt coated with a 0.1 mm thick 4 cm$^2$ patch of carnauba wax with a dye dissolved there so that after two weeks at 30° C. and 40% relative humidity, there is not more than a 15% gain in surface area with visible oil stain or coloration thereon. Preferably there is no more than a 5% gain in stained or colored surface area.

Even when the paper substrate is treated to prevent migration of colorants, additional effects can cause other types of smearing on the samplers. The samplers are often found as inserts in magazines or provided as an array of samplers stacked in a pad with one of its edges adhesively secured so that the samplers can be distributed one at a time. These physical environments can place stresses and particularly shearing forces on the cosmetic sample itself which will cause it to smear. This can particularly happen at higher ambient temperatures such as 35° to 40° C.

It has been found according to the present invention that a thin, frangible film of a polymer can be applied over the surface of the cosmetic material to prevent it from being smeared, yet enable it to be transferred easily to the skin. The film preferably has a breaking strength of less than 2.5 kilograms per cm of width. Preferably the film should have a breaking strength of less than 1.5 kg/cm width, more preferably less than 1.0 kg/cm width, and most preferably less than 0.7 kg/cm width. The film should have a minimum strength of at least 0.02 kg/cm width.

The film can be applied generally over the sampling surface, covering the cosmetic and the substrate. It can be applied by spraying, extrusion, lamination, or any other conventional method. The film is applied generally at a dry coating weight of between $10^{-4}$ and $10^{-2}$ g/cm$^2$. Preferably it is coated at a weight between $2 \times 10^{-4}$ and $5 \times 10^{-3}$ g/cm$^2$. This approximates a thickness of between about 0.75 and 20 microns, preferably between about 1 and 12 microns. This will vary a good deal depending upon the physical properties of the polymer chosen.

Preferably the polymer is a hydrophilic polymer. Preferred compositions are ethylene maleic anhydride copolymers and copolymers with methyl vinyl ether, or monoalkyl esters (e.g., $C_1$ to $C_5$) of the maleic anhydride polymers or copolymers. Cellulose acetate esters (e.g., cellulose acetate butyrate and proprionate), poly(N-methyl vinylpyrollidone), ethylcellulose, polyacrylates, hydroxypropylcellulose, and the like. The cellulosic polymers and ethylene maleic anhydride polymers and copolymers are preferred.

The polymeric film should be brittle if possible so that there is a reduced tendency of the covering film to "skin" or be removed as a film. The lipstick should be removable as a waxy material rather than as a mixture of film and wax. The brittleness and thinness of the film contribute to this.

One additional problem has been encountered in the use of paper, even with oleophobic penetrating compositions. The composition renders the paper surface oleophobic so that there is a poor bond established between the cosmetic composition and the paper. Although the entire cosmetic composition layer does not release from the substrate, small patches of the composition can be removed. This gives an unsightly appearance to the sampler.

It has been found that a primer coating over said treated paper surface can overcome this adhesion problem and not increase the discoloration effect if the primer is an oleophilic wax or polymer and the coating has a thickness of between 0.5 and 50 microns, preferably between 0.5 and 10 microns. Oleophilic waxes such as carnauba wax, beeswax, candlewax, and the like may be used. Particularly desirable polymers include poly(N-vinylpyrrolidone), polyacrylates (e.g., polymethylmethacrylate, poly-n-butylmethacrylate), cellulose esters (e.g., cellulose acetate butyrate, cellulose acetate proprionate), poly(vinyl alcohol) and the like. Hydroxyalkylcellulose work less preferably. These materials are preferably coated out as low concentration solutions (e.g., 1 to 20% by weight, preferably 1 to 8% by weight) in order to insure a thin coating on the surface. Printing inks and varnishes may also act as primer coatings on the paper.

Control of the thickness of the coating, especially keeping the coating equal to or less than 50 microns is believed to be important in preventing the primer from laterally transmitting any dye. It is preferred that the coating be 25 microns or less, and more preferred that it be 10 microns or less.

Cosmetic samples are usually to be provided in either single folded or overlayed sheets of as an insert or page or a magazine or brochure. The oleophobic surface or layer which is in contact with the solid cosmetic composition layer can be loosely (i.e., strippably) adhered to the surface of the composition, overlaid on the cosmetic material (held in place by a face of the folded sheet or magazine page), or adhered to a facing (opposite) page. The oleophilic layer may be easily strippably adhered to the cosmetic material. If the cosmetic composition is applied as a hot melt or dryable composition, the oleophilic layer may be laid on top contemporaneously with that application. The layer may also be placed on an opposed surface and heated, or used with a moderate- or low-strength pressure-sensitive adhesive, after application of the layer to the paper base.

The oleophobic penetrating composition can be selected from a number of commercially available types of materials such as fluorocarbons (e.g., Scotchban TM, a salt of a highly fluorinated polymer or a fluorochemical phosphate ester) and fluorochemical phosphates. Other materials such as fluorinated polymers and compositions such as those described in U.S. Pat. No. 4,529,658 are also useful. The disclosure of that patent is incorporated herein by reference with respect to the compositions and disclosure of chemical materials described therein. The preferred composition is a fluorochemical polymer, particularly those derived from about 60 to 80% of fluorochemical acrylates, 1 to 30% alkyl or alkoxyalkyl acrylates (inclusive also of methacrylates), 2 to 15% glycidyl acrylate (inclusive also of methacrylates), 1 to 6% cationic acrylates (inclusive also of methacrylates) and 0 to 20% vinylidene chloride. These materials are used in amounts of 0.002 to 3% by weight of paper in the base, preferably 0.02 to 2% by weight of said paper. Other fluorochemical polymers are used in the same weight ratios.

The oleophobic surface may be a film, laminated film, coated surface, foil, metallized surface, and the like. Many polymeric materials are useful for the film including but not limited to acrylates, polyamides, polyvinyl resins/polyvinyl alcohol, polyvinylidene chloride, polyvinyl chloride, silicon resins, and the like.

The cosmetic compositions are limited to those containing at least 5% by weight of an emollient or wax material. Compositions with lower contents of these oleic materials do not need to practice the present invention. Other conventional cosmetic additives may of course be present in the cosmetic layer. Such materials as polymeric binders, oils, water, dyes, pigments, moisturizers, fragrances, filler, antioxidants, emulsifying agents, and the like are often present.

The cosmetic composition is preferably applied to the sampler in sufficient quantity so that it may be transferred to a person's skin in amounts that will approximate normal usage of the cosmetic. Coating thicknesses of at least 10 microns and more preferably at least 50 microns are desirable. Coating thicknesses in the range of 0.01 to 0.3 mm and preferably 0.02 to 0.1 mm are generally used.

Stacks of sampler sheets are strippably adhered together at the edges or through the cosmetic material as an adhesive. This last construction can be effected by having the backside of the upper samples, in contact with the cosmetic coating layer, coated with or laminated to the oleophobic layer.

These and other aspects of the present invention will be described in the following non-limiting examples.

EXAMPLE 1

Two sheets of two-side coated printing stock were used in this example. The paper is coated on both sides with a clay and polymer coating composition. Both sheets of paper were treated with 1% by weight of the paper of Scotchban TM oil repellent, an oligomeric fluorinated ester. Both the coating and the paper itself absorbed the oil repellent. One coated surface of both coated sheets was coated with a 1 mil ($2.5 \times 10^{-5}$ m) wet thickness coating of a 3% solids solution of poly(N-vinyl pyrollidone) and oven dried at 105° C. This produced a coating of average thickness between 0.5 and 1 microns. A stick of commercially available wax base lipstick was gently melted and hand coated onto one surface of each of the paper bases. Over one of the lipstick samples was coated at $2.5 \times 10^{-5}$ m wet thickness a 3% by weight solids solution of a monomethyl ester of ethylene maleic acid copolymer (EMA TM 21, Monsanto Corp.) in 27% methanol, 40% ethanol and 30% methylene chloride. The sample was dried at 50°–75° C. for two minutes. This procedure was duplicated with the uncoated cosmetic sample and the two samples stored for two weeks at 25°–30° C. under a pressure of about 4 kg/cm$^2$.

No stain could be seen in either of the samples. The sample with the copolymer film coating released the lipstick onto one's fingers without completely lifting off the paper. The uncoated treated sample allowed some portions of the lipstick layer to adhere to the opposed surface.

What is claimed is:

1. A multilayered structure for sampling cosmetic compositions comprising a paper base having an oleophobic agent within said paper, a solid cosmetic composition layer containing a wax or emollient component on at least a portion of one surface of said paper base and said structure being characterized by the presence of a thin, frangible oleophilic film coating over said solid cosmetic composition layer.

2. The structure of claim 1 wherein said paper has an oleophilic coating comprised of an oleophilic wax or oleophilic polymeric resin, and said cosmetic composition comprises lipstick.

3. The structure of claim 1 having an oleophobic layer in contact with said solid cosmetic composition layer.

4. The structure of claim 3 wherein said oleophobic agent is throughout the paper base.

5. The structure of claim 3 wherein said paper base comprises paper coated with pigment and binder.

6. The structure of claim 5 wherein said oleophobic agent is present within said paper and said coating of pigment and binder.

7. The structure of claim 2 wherein said oleophobic agent is a fluorocarbon and said oleophilic film coating has a thickness between 0.75 and 20 microns.

8. The structure of claim 4 wherein said oleophobic agent is a fluorocarbon and said oleophilic film coating has a thickness between 1 and 12 microns and a breaking strength of less than 1.5 kg/cm width.

9. The structure of claim 5 wherein said oleophobic agent is a fluorocarbon and said oleophilic coating has a thickness between 0.75 and 10 microns.

10. The structure of claim 6 wherein said oleophobic agent is a fluorocarbon and said oleophilic coating has a thickness between 0.5 and 25 microns.

11. The structure of claim 2 wherein said oleophilic film comprises a thin frangible film having a thickness of between 0.75 and 20 micrometers.

12. The structure of claim 2 wherein said oleophilic film has a breaking strength of less than 2.5 kg/cm of width.

13. The structure of claim 3 wherein said oleophilic film has a weight of between 0.05 and 15 g/cm$^2$.

14. The structure of claim 2 wherein said oleophilic film comprises a polymer or copolymer of ethylene maleic anhydride.

15. The structure of claim 9 wherein said oleophilic film comprises a polymer or copolymer of ethylene maleic anhydride.

16. The structure of claim 5 wherein said oleophobic surface is a paper base with an oleophobic polymeric composition thereon comprising a fluorinated polymer or phosphate ester of a fluorinated polymer.

17. The structure of claim 5 wherein said oleophobic surface is a paper base with an oleophobic polymeric composition thereon.

18. The structure of claim 2 wherein said oleophobic surface is a paper base with an oleophobic polymeric composition thereon comprising by weight
60 to 80% fluorochemical acrylate,
1 to 30% alkyl- or alkoxyalkyl-acrylate,
2 to 15% glycidyl acrylate,
1 to 6% cationic acrylate, and
0 to 20% vinylidene chloride.

19. The structure of claim 11 wherein said oleophobic surface is a paper base with an oleophobic polymeric composition thereon comprising by weight
60 to 80% fluorochemical acrylate,
1 to 30% alkyl- or alkoxyalkyl-acrylate,
2 to 15% glycidyl acrylate,
1 to 6% cationic acrylate, and
0 to 20% vinylidene chloride.

20. The structure of claim 19 wherein said polymeric film comprises a polymer or copolymer of ethylene maleic anhydride.

21. A multilayered structure for sampling cosmetic compositions comprising a paper base having an oleophobic agent within said paper, a solid cosmetic lipstick composition layer containing a wax or emolient component on at least a portion of one surface of said paper base and said structure being characterized by the presence of a thin, frangible oleophilic film coating over said solid cosmetic composition layer, said thin oleophilic film coating having a thickness of between 0.75 and 20 microns and a breaking strength of less than 2.5 kg/cm width.

22. The structure of claim 2 wherein said paper has an oleophilic coating comprised of an oleophilic wax or oleophilic polymeric resin.

* * * * *